United States Patent [19]

Williams

[11] Patent Number: 5,625,196
[45] Date of Patent: Apr. 29, 1997

[54] METHOD AND APPARATUS FOR MONITORING/CALIBRATING A PROCESS MEASURING SYSTEM

[75] Inventor: Paul Williams, Columbus, Ohio

[73] Assignee: ABB Industrial Systems, Inc., Columbus, Ohio

[21] Appl. No.: 453,272

[22] Filed: May 30, 1995

[51] Int. Cl.$^6$ .................................................. G01N 21/86
[52] U.S. Cl. ................... 250/559.1; 250/559.45; 250/205
[58] Field of Search ................... 250/559.1, 205, 250/208.5, 559.45; 356/4.01, 141.1–141.4

[56] References Cited

U.S. PATENT DOCUMENTS

| | | | |
|---|---|---|---|
| 4,098,641 | 7/1978 | Casey et al. | 162/198 |
| 4,289,406 | 9/1981 | Maddox | 356/429 |
| 4,767,935 | 8/1988 | Anderson et al. | 250/559.46 |
| 4,950,911 | 8/1990 | Williams et al. | 356/237 |
| 4,954,891 | 9/1990 | Burk et al. | 362/223 |
| 5,019,710 | 5/1991 | Wennerberg et al. | 250/341 |
| 5,071,514 | 12/1991 | Francis | 162/259 |
| 5,149,952 | 9/1992 | Tanaka et al. | 250/559.1 |
| 5,166,510 | 11/1992 | Matsubara et al. | 250/205 |
| 5,243,407 | 9/1993 | King et al. | 356/429 |
| 5,395,027 | 3/1995 | Erhardt | 226/24 |
| 5,502,312 | 3/1996 | Lorenzo | 250/205 |

FOREIGN PATENT DOCUMENTS 2087544  5/1982  United Kingdom .

Primary Examiner—Que Le
Attorney, Agent, or Firm—Killworth, Gottman, Hagan & Schaeff

[57] ABSTRACT

A detector of a measuring system sensitive to light energy receives light from a process being measured and also from a separate light source which is modulated such that it can be detected in signals generated by the detector. The separate light source is turned on and off to modulate its output such that output signals from the detector can be separated into on-times and off-times of the separate light source. The difference in on and off signal levels generated by the detector, or elements of the detector if the detector has a plurality of elements, are used to calibrate the detector. The light energy is conveyed to the detector by an energy conduit which may be a "leaky" optical fiber which receives light at one end and leaks the light out one sidewall along a portion of the fiber which is positioned adjacent to and preferably secured to the detector. The leaky optical fiber can be made by removing cladding from at least a portion of the sidewall along the portion of the fiber which is to leak light to the detector. Alternately, a bundle of fiber optics can be utilized with one end of the bundle receiving light and the other end being broken out to direct one or more of the fibers toward elements of the detector.

20 Claims, 1 Drawing Sheet

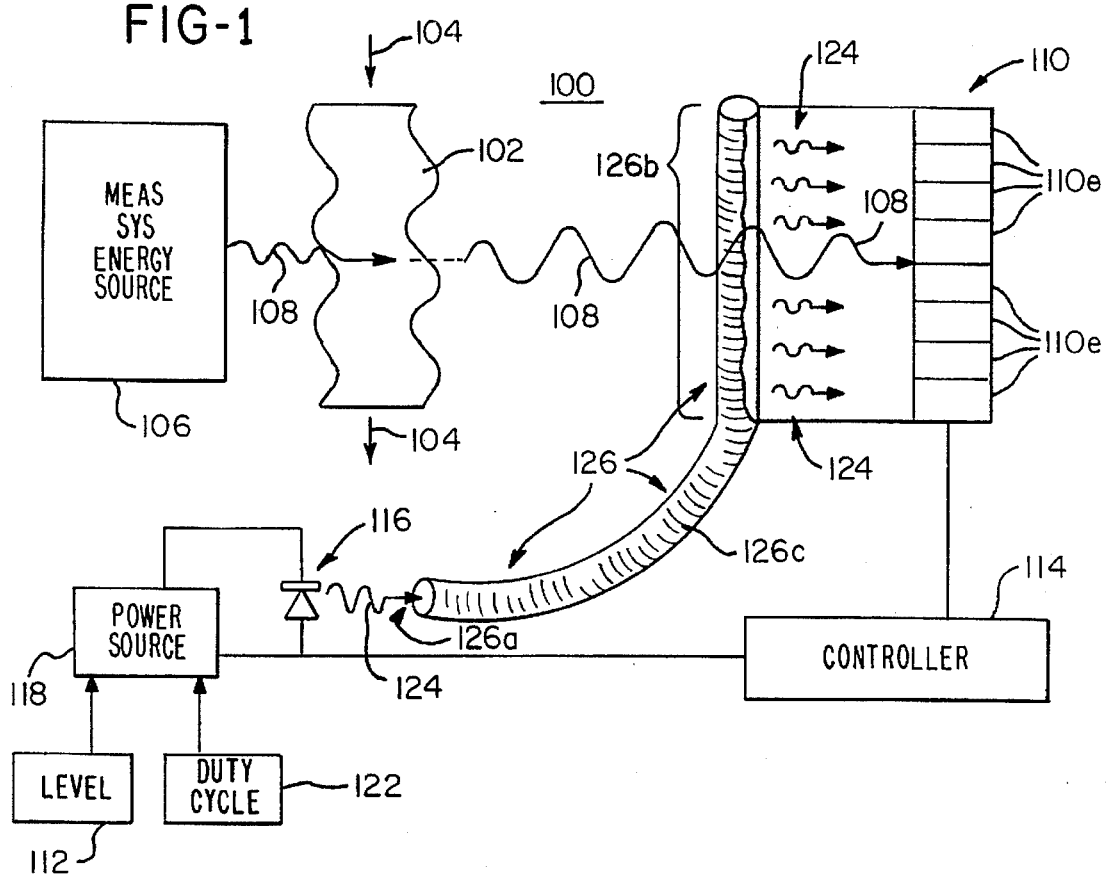
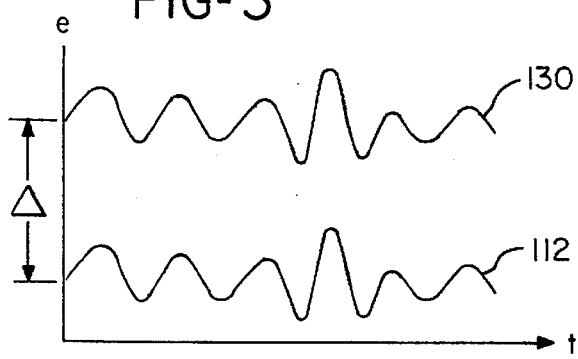
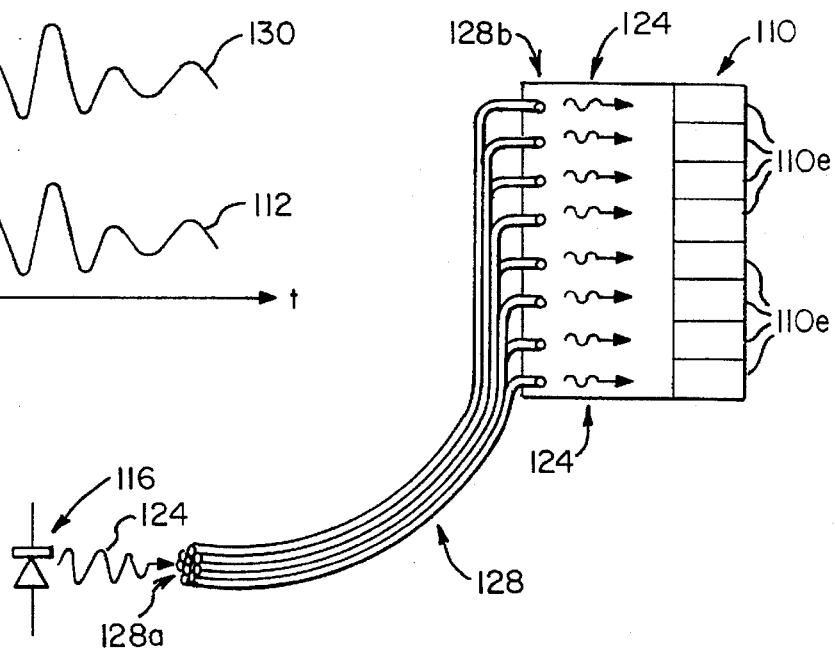

METHOD AND APPARATUS FOR MONITORING/CALIBRATING A PROCESS MEASURING SYSTEM

BACKGROUND OF THE INVENTION

The present invention relates in general to the production of a web of sheet material commonly referred to as a "process" and, more particularly, to a method and apparatus for monitoring and/or calibrating a detector used in measuring one or more characteristics of the process as it is being produced.

In the art of making sheet material, such as paper, coated paper, plastics and the like, it is important to monitor various characteristics of the sheet material or process which is typically manufactured as a relatively fast moving web. Monitoring systems in turn must be monitored and frequently calibrated to provide accurate information for controlling manufacture of the process.

One currently popular form of monitoring webs of sheet material traveling in a direction referred to as the machine direction, is to physically move a monitoring gauge across the web in a direction referred to as the cross direction which is substantially perpendicular to the machine direction. For calibration purposes, movement of a scanning gauge is continued to move the gauge off the process being monitored to a position where it can be exposed to a set of standard conditions, such as a process sample having known characteristics. It is apparent that such scanning measurement ignores the majority of the web since only the material along a zig-zag line is monitored by the traveling gauge. The amount of material which is monitored is further reduced by performing off-process calibration.

In an attempt to more fully monitor a process being manufactured and to speed up web measurement and control, a stationary optical sensor extending continuously across a paper web is disclosed in U.S. Pat. No. 5,071,514. As disclosed in the '514 patent, the stationary optical sensor is calibrated by a closely associated scanning optical sensor which senses discrete regions of the web as it is scanned across the web.

In this arrangement, the stationary sensor can be calibrated on-line using the scanning sensor. The scanning sensor can itself be calibrated off-line, i.e. off the process being measured, without impacting current operation of the stationary sensor. Unfortunately, provision of both a stationary sensor and a scanning sensor is very expensive and complicates the structure and operation of the overall measurement system.

Accordingly, there is a need for an effective and inexpensive arrangement for monitoring and/or calibrating on-line process measuring systems without interrupting the collection of process data. Such a monitoring and/or calibrating arrangement is ultimately required for a commercially viable stationary, non-scanning sensor for a process monitoring system.

SUMMARY OF THE INVENTION

This need is met by the method and apparatus of the present invention wherein a detector of a measuring system sensitive to a given form of energy, such as light energy, receives energy from a process being measured and also from a separate energy source which is modulated such that it can be detected in signals generated by the detector. Preferably, the separate energy source is turned on and off to modulate its output such that output signals from the detector can be separated into times when the separate energy source was on and times when the separate energy source was off. By determining the difference in signal levels for the detector, or each element of the detector in the case of a detector having a plurality of elements, the detector can be calibrated by comparing signals generated when the separate energy source is on to signals generated when the separate energy source is off. The resulting difference signals define detector operation and are used to calibrate the detector or detector elements.

The energy level of the separate source can be made sufficiently low that when it is on it does not impact control of the process. However, it is preferred to ignore such modified signals or remove them from the data stream being used to control the process. Due to the large amounts of data which are collected in stationary, non-scanning sensors, the removal of small portions of collected data have no impact on the quality of control provided for the process.

Apparatus in accordance with the present invention includes a source of modulated power which drives an energy source for generating detector sensitive energy and an energy conduit for conveying the energy to the detector. In an illustrated embodiment of the invention, light energy is utilized and the energy conduit may comprise a "leaky" optical fiber which receives light at one end and leaks the light out one sidewall along a portion of the fiber which is positioned adjacent to and preferably secured to the detector. Such a leaky optical fiber can be made by removing cladding from at least a portion of the sidewall along the portion of the fiber which is to leak light to the detector. Alternately, a bundle of fiber optics can be utilized with one end of the bundle receiving light and the other end being broken out to direct one or more of the fibers toward each element of the detector.

In accordance with one aspect of the present invention, a method of monitoring a detector of a system for measuring one or more characteristics of a process without interrupting measurement operations of the system comprises the steps of: directing detector sensitive energy onto the detector; modulating the detector sensitive energy with a defined modulation; and, detecting the defined modulation in measurement signals generated by the detector. For one form of detector, the step of directing detector sensitive energy onto the detector comprises the step of illuminating the detector with light energy. Preferably, the step of modulating the detector sensitive energy comprises the step of selectively activating and deactivating a source of the detector sensitive energy. For example, the step of modulating the detector sensitive energy may comprise the step of controlling the duty cycle of the detector sensitive energy directed onto the detector, preferably to approximately 0.1 percent of the duty cycle of the energy.

The method may further comprise the steps of: determining the amplitudes of detected defined modulation; providing expected amplitudes for detected defined modulation; and, comparing determined amplitudes of detected defined modulation to expected amplitudes for detected defined modulation to generate detector response signals. The detector response signals may then be used to perform the step of calibrating the detector.

In accordance with another aspect of the present invention, apparatus for monitoring a detector of a system for measuring one or more characteristics of a process without interrupting the measurement operations of the system comprises an energy source for generating energy of a type used in the measuring system and a power source for driving the energy source. A modulator modulates the power source with the resulting modulated energy being carried to the detector of the measuring system via an energy conduit while the measuring system is performing measurement operations.

In accordance with yet another aspect of the present invention, apparatus for monitoring a detector of a system for measuring one or more characteristics of a process without interrupting the measurement operations of the system comprises an energy source for generating energy of a type used in the measuring system and a power source for driving the energy source. A modulator is provided for controlling the output level of the power source and an on/off duty cycle of the power source. An energy conduit carries energy generated by the energy source to the detector of the measuring system while the measuring system is performing measurement operations. A controller synchronized with the modulator accumulates output signals from the detector of the measuring system during periods of time corresponding to on-times of the power source and during periods of time corresponding to off-times of the power source.

The controller further provides for comparing on-time accumulated output signals to off-time accumulated output signals to generate detector characteristic signals. If the detector of the measuring system comprises a plurality of detector elements, the controller accumulates the output signals for each of the detector elements to generate characteristic signals for each of the plurality of detector elements.

For light sensitive detectors, the energy source may comprise a light emitting diode (LED). In any event, where light energy is utilized, the energy conduit may comprise a fiber optic having a light receiving end positioned adjacent the light source and a light dispensing end positioned adjacent the detector, the light dispensing end comprising a length of the fiber optic having a sidewall through which light passes to impinge on the detector of the measuring system. Light passage through the sidewall can be enhanced when the fiber optic includes an outer clad by removing at least a portion of the clad along the length of the fiber optic defining the light dispensing end.

Alternately, the energy conduit may comprise a bundle of fiber optics having a light receiving end positioned adjacent the light source and a light dispensing end positioned adjacent the detector for directing light on the detector of the measuring system. Preferably, the energy conduit is secured to the detector for delivering energy generated by the energy source without interfering with measurement operations performed by the measuring system.

It is, thus, an object of the present invention to provide an improved method and apparatus for monitoring and/or calibrating a system used to measure one or more characteristics of a web of sheet material as the web is being manufactured; to provide an improved method and apparatus for monitoring and/or calibrating a process measuring system by directing modulated energy onto a detector of the measuring system during operation of the system such that the modulated energy can be detected and used to monitor and/or calibrate the detector; and, to provide an improve method and apparatus for monitoring and/or calibrating a light sensitive detector of a process measuring system by directing modulated light energy to the detector via a "leaky" optical fiber or a bundle of fiber optics during normal operation of the measuring system.

Other objects and advantages of the invention will be apparent from the following description, the accompanying drawings and the appended claims.

BRIEF DESCRIPTION OF THE DRAWINGS

FIG. 1 is a schematic block diagram of a process measuring system including apparatus structured and operable in accordance with the present invention for monitoring and/or calibrating the measuring system without interrupting the system's operation;

FIG. 2 illustrates an alternate embodiment of an energy conduit for conveying modulated energy from the energy source to the detector of FIG. 1; and FIG. 3 is a graph representing detected energy output generated by the detectors of FIGS. 1 and 2 when illuminated only by the measurement system energy source and when illuminated by both the measurement system energy source and the separate energy source of the monitoring/calibrating arrangement of the present invention.

DETAILED DESCRIPTION OF THE INVENTION

The invention of the present application will now be described with reference to FIG. 1 which schematically illustrates a stationary non-scanning system 100 for measuring one or more characteristics of a web of sheet material, commonly referred to as a process 102, as the process 102 is being manufactured. For example, the process 102 may be a web of sheet paper which is moving in the direction of the arrows 104 as it progresses from a pulp slurry at the beginning end of a paper making machine to a paper web at the finished end of the machine.

Machines for making webs of sheet material, such as paper, and stationary non-scanning systems for measuring characteristics of webs of sheet material as they are being manufactured are well known in the art and will be described herein only to the extent necessary to understand the present invention. Those desiring additional information regarding details of such machines and measuring systems are referred to U.S. Pat. No. 5,071,514 which is incorporated herein by reference.

As shown in FIG. 1, the web measuring system 100 comprises a measurement system energy source 106. Energy sources used in web measuring systems range from sources of beta particles to sources of light energy selected within broad or narrow bands of light frequencies. In the embodiment illustrated in FIG. 1, the energy source 106 emits light energy 108 which passes through the process 102 and is received by a detector 110 which comprises a detector array made up of a plurality of detector elements 110e. The attenuation of the light energy 108 by the process 102 reveals characteristics of the process 102 such as basis weight, moisture content and the like which are to be measured.

The detector elements 110e of the detector 110 generate signals such as a signal 112, shown in FIG. 3, which are passed to a controller 114. The controller 114 forms part of the measuring system 100 in the illustrated embodiment and is used to process the signals received from the detector 110 to measure characteristics of the process 102 and control a machine which is making the process to maintain required process quality. In the past, such detectors have been calibrated on-line by means of a closely associated scanning optical sensor which senses discrete regions of the process 102 as it is scanned across the process 102. Unfortunately, provision of both a stationary non-scanning sensor and a scanning sensor is very expensive and complicates the structure and operation of the overall measurement system.

In accordance with the present invention, monitoring and/or calibration of the measuring system 100 is simplified by provision of a separate energy source which is modulated to provide modulated energy to the detector 110 above and beyond the energy received from the measurement system energy source 106. The separate energy source is illustrated in FIG. 1 as a light emitting diode (LED) 116 which is driven by a power source 118, of course other energy sources can be used in the present invention. The output power level of the power source 118 is set by a level control circuit 120 which can be internal to the source 118. The power source is preferably cycled on and off to define a duty cycle of off-time to on-time which is controlled by a duty cycle circuit 122 which also can be internal to the source 118.

Light energy 124 generated by the energy source LED 116 is carried by an energy conduit to the detector 110 of the measuring system 100 while the measuring system 100 is performing measurement operations. In the illustrated embodiment of FIG. 1, the energy conduit comprises a fiber optic 126 having a light receiving end 126a positioned adjacent the LED 116 and a light dispensing end 126b positioned adjacent the detector 110. The light dispensing end 126 comprises a length of the fiber optic 126 having a sidewall through which light passes to impinge on the detector 110 of the measuring system 100.

Preferably, the fiber optic 126 includes an outer clad 126c and the length of the fiber optic 126 defining the light dispensing end 126b has at least a portion of the clad 126c removed therefrom. As illustrated in FIG. 1, the clad 126c is removed along that portion of the sidewall of the light dispensing end 126b which faces the detector 110. Alternately, as shown in FIG. 2, the energy conduit may comprise a bundle 128 of fiber optics having a light receiving end 128a positioned adjacent the LED 116 and a light dispensing end 128b positioned adjacent the detector 110 for directing light on the detector 110 of the measuring system 100.

The energy conduit, illustrated as the fiber optic 126 or the bundle 128 of fiber optics in FIGS. 1 and 2 respectively, are preferably secured to the detector 110 and are positioned such that they deliver energy to the detector 110 without interfering with the energy delivered to the detector 110 from the measuring system energy source 106 after passage through the process 102. In this way, the monitoring/calibrating arrangement of the present invention can be operated during normal operation of the measuring system 100. Structural details regarding the coupling of the energy conduit to the detector 110 depend upon the particular design of the detector 110 and will not be described herein.

By controlling the duty cycle of the power source 118 via the duty cycle circuit 122, light energy 124 from the LED 116 can be added at defined intervals to the light energy 108 from the measuring system energy source 106 which has been modulated by the process 102. During periods of time that light energy 124 from the LED 116 is added, there is an energy differential $\Delta$ detectable in the signals generated by the detector 110 or each of the detector elements 110e as represented by the signal 130 in FIG. 3. In the illustrated embodiment of the invention, the controller 114 determines the energy differential $\Delta$ and is connected to the power source 118 for synchronization with the modulation of the output power from the power source 118.

As shown in FIG. 3, the differential $\Delta$ is a constant across the entire detector 110; however, it should be apparent that the actual differential $\Delta$ can vary along the length of the detector 110 or for each of the detector elements 110e. Such differences do not matter since the calibration process takes these difference into account.

In particular, the detector 110 or detector elements 110e are exposed to a series of standard conditions, such as samples of the process 102 having known characteristics, and correction factors are computed which calibrate, normalize or standardize the response or signals generated by the detector 110 or detector elements 110e. One or more of the standard conditions is illuminated by the light energy 124 from the LED 116 which can be repeated while measurements are being made by the measuring system 100. These measurements provide a measure of the response of the detector 100 or detector elements 110e such that calibration, normalization or standardization can be performed.

The continuous energy output from the separate energy source or LED 116 in combination with the energy from the measuring system energy source 106 should be less than required to saturate the detector 110 or any one of the detector elements 110e. The energy level of the separate source or LED 116 can be made sufficiently low that when it is on it does not substantially impact control of the process. However, it is preferred to ignore signals modified by input from the separate energy source or remove the modified signals from the data stream being used to control the process. Due to the large amounts of data which are collected in stationary, non-scanning sensors, the removal of small portions of collected data has no impact on the quality of control provided for the process.

Thus, signals generated by the detector 110 or detector elements 110e during the on portion of the duty cycle of the power source 118 are accumulated and signals generated during the off portion of the duty cycle are accumulated. The accumulation of signals made during the on portion of the duty cycle are compared to the accumulation of signals made during the off portion of the duty cycle to monitor and/or calibrate the detector 110 or detector elements 110e.

Having thus described the invention of the present application in detail and by reference to preferred embodiments thereof, it will be apparent that modifications and variations are possible without departing from the scope of the invention defined in the appended claims.

What is claimed is:

1. A method of monitoring a detector of a system for measuring one or more characteristics of a process without interrupting measurement operations of the system wherein measuring system energy is directed upon said detector for performing said measurement operations, said method comprising the steps of:

directing detector sensitive energy above and beyond said measuring system energy onto said detector;

modulating said detector sensitive energy with a defined modulation which can be detected in measurement signals generated by the detector; and detecting said defined modulation in measurement signals generated by said detector.

2. The method of claim 1 wherein the step of directing detector sensitive energy onto said detector comprises the step of illuminating said detector with light energy.

3. The method of claim 1 wherein the step of modulating said detector sensitive energy comprises the step of selectively activating and deactivating a source of said detector sensitive energy.

4. The method of claim 1 wherein the step of modulating said detector sensitive energy comprises the step of controlling the duty cycle of the detector sensitive energy directed onto said detector.

5. The method of claim 4 wherein the step of modulating said detector sensitive energy comprises the step of controlling the duty cycle of the detector sensitive energy directed onto said detector to approximately 0.1 percent of the duty cycle of said energy.

6. The method of claim 1 further comprising the steps of:
   determining the amplitudes of detected defined modulation;
   providing expected amplitudes for detected defined modulation; and
   comparing determined amplitudes of detected defined modulation to expected amplitudes for detected defined modulation to generate detector response signals.

7. The method of claim 6 further comprising the step of calibrating said detector based on said detector response signals.

8. Apparatus for monitoring a detector of a system for measuring one or more characteristics of a process without interrupting the measurement operations of the system which includes a measuring system energy source for generating energy used in the system, said apparatus comprising:
   an energy source separate from said measuring system energy source for generating energy of a type used in said measuring system;
   a power source for driving said separate energy source;
   a modulator for modulating said power source; and
   an energy conduit for carrying energy generated by said separate energy source to the detector of said measuring system while said measuring system is performing measurement operations.

9. Apparatus as claimed in claim 8 wherein said separate energy source comprises a light emitting diode.

10. Apparatus as claimed in claim 8 wherein said separate energy source comprises a light source and said energy conduit comprises a fiber optic having a light receiving end positioned adjacent said light source and a light dispensing end positioned adjacent said detector, said light dispensing end comprising a length of said fiber optic having a sidewall through which light passes to impinge on the detector of said measuring system.

11. Apparatus as claimed in claim 10 wherein said fiber optic includes an outer clad and said length of said fiber optic defining said light dispensing end has had at least a portion of said clad removed therefrom.

12. Apparatus as claimed in claim 8 wherein said separate energy source comprises a light source and said energy conduit comprises a bundle of fiber optics having a light receiving end positioned adjacent said separate light source and a light dispensing end positioned adjacent said detector for directing light on the detector of said measuring system.

13. Apparatus as claimed in claim 8 wherein said energy conduit is secured to said detector for delivering energy generated by said energy source without interfering with measurement operations performed by said measuring system.

14. Apparatus for monitoring a detector of a system for measuring one or more characteristics of a process without interrupting the measurement operations of the system which includes a measuring system energy source for generating energy used in the system, said apparatus comprising:
   an energy source separate from said measuring system energy source for generating energy of a type used in said measuring system;
   a power source for driving said separate energy source;
   a modulator for controlling the output level of said power source and an on/off duty cycle of said power source;
   an energy conduit for carrying energy generated by said separate energy source to the detector of said measuring system while said measuring system is performing measurement operations; and
   a controller synchronized with said modulator for accumulating output signals from said detector of said measuring system during periods of time corresponding to on-times of said power source and during periods of time corresponding to offtimes of said power source.

15. Apparatus as claimed in claim 14 wherein said separate energy source comprises a light emitting diode.

16. Apparatus as claimed in claim 14 wherein said controller further provides for comparing on-time accumulated output signals to off-time accumulated output signals to generate detector characteristic signals.

17. Apparatus as claimed in claim 16 wherein said detector of said measuring system comprises a plurality of detector elements and said controller accumulates said output signals for each of said detector elements to generate characteristic signals for each of said plurality of detector elements.

18. Apparatus as claimed in claim 17 wherein said separate energy source comprises a light source and said energy conduit comprises a fiber optic having a light receiving end positioned adjacent said separate light source and a light dispensing end positioned adjacent said detector, said light dispensing end comprising a length of said fiber optic having a sidewall through which light passes to impinge on the detector of said measuring system.

19. Apparatus as claimed in claim 18 wherein said fiber optic includes an outer clad and said length of said fiber optic defining said light dispensing end has had at least a portion of said clad removed therefrom.

20. Apparatus as claimed in claim 17 wherein said separate energy source comprises a light source and said energy conduit comprises a bundle of fiber optics having a light receiving end positioned adjacent said light source and a light dispensing end positioned adjacent said detector for directing light on the detector of said measuring system.

* * * * *

UNITED STATES PATENT AND TRADEMARK OFFICE
CERTIFICATE OF CORRECTION

PATENT NO. : 5,625,196
DATED : April 29, 1997
INVENTOR(S) : Paul Williams

It is certified that error appears in the above-indentified patent and that said Letters Patent is hereby corrected as shown below:

Column 8, line 23, "offtimes" should be --off-times--.

Signed and Sealed this

Seventh Day of October, 1997

Attest:

BRUCE LEHMAN

Attesting Officer

Commissioner of Patents and Trademarks